United States Patent
Hofman et al.

(10) Patent No.: US 7,399,971 B2
(45) Date of Patent: Jul. 15, 2008

(54) SINGLE-POINT MEASUREMENT OF HIGH-Z ADDITIVES IN SHEETS

(75) Inventors: Gertjan J. Hofman, North Vancouver (CA); Reena Meijer Drees, New Westminster (CA)

(73) Assignee: Honeywell International Inc., Morristown, NJ (US)

( * ) Notice: Subject to any disclaimer, the term of this patent is extended or adjusted under 35 U.S.C. 154(b) by 217 days.

(21) Appl. No.: 11/317,693

(22) Filed: Dec. 23, 2005

(65) Prior Publication Data

US 2007/0145286 A1 Jun. 28, 2007

(51) Int. Cl.
*G01F 23/00* (2006.01)
(52) U.S. Cl. .................................... 250/358.1
(58) Field of Classification Search ............... 250/358.1
See application file for complete search history.

(56) References Cited

U.S. PATENT DOCUMENTS

| | | | | |
|---|---|---|---|---|
| 4,037,104 A | | 7/1977 | Allport | |
| 5,247,177 A | * | 9/1993 | Goldberg et al. | 250/358.1 |
| 5,325,416 A | * | 6/1994 | Saito et al. | 378/50 |
| 5,720,739 A | * | 2/1998 | Hilston et al. | 604/390 |
| 5,778,041 A | | 7/1998 | Chase et al. | |
| 5,930,314 A | * | 7/1999 | Lanza | 376/159 |
| 6,168,687 B1 | * | 1/2001 | Hu et al. | 162/198 |
| 6,362,477 B1 | * | 3/2002 | Sowerby et al. | 250/358.1 |
| 6,377,652 B1 | | 4/2002 | Sturm | |
| 7,009,181 B1 | * | 3/2006 | Miller et al. | 250/358.1 |
| 7,220,967 B1 | * | 5/2007 | Shapiro et al. | 250/358.1 |
| 2003/0007158 A1 | * | 1/2003 | Hill | 356/493 |
| 2006/0043304 A1 | * | 3/2006 | Miller et al. | 250/358.1 |
| 2007/0145286 A1 | * | 6/2007 | Hofman et al. | 250/394 |

FOREIGN PATENT DOCUMENTS

| | | |
|---|---|---|
| EP | 0112079 A2 | 6/1984 |
| EP | 0141751 A2 | 5/1985 |
| EP | 0228147 A2 | 7/1987 |
| JP | 02088462 A * | 3/1990 |

* cited by examiner

*Primary Examiner*—David P. Porta
*Assistant Examiner*—Kiho Kim
(74) *Attorney, Agent, or Firm*—Scully, Scott, Murphy & Presser PC

(57) ABSTRACT

An apparatus, method and computer program product for determining a concentration of a high-Z material in a material sample. The method comprises steps of: receiving a material sample and subjecting the material sample to a first sensor device that is substantially ash insensitive for generating a first sensor response signal, and a second sensor device that is sensitive to presence of high-Z material and generating a second sensor response signal. Both the first and second sensor response signals from the first and second sensor devices are processed simultaneously to extract a weight of the high-Z material additive. The weight of the high-Z material additive is determined in a single scan of the material sample.

16 Claims, 4 Drawing Sheets

SINGLE-POINT MEASUREMENT OF HIGH-Z ADDITIVES IN SHEETS

FIELD OF THE INVENTION

The present invention relates generally to techniques for determining compositions of materials, and, particularly, a novel single-point measurement system for measuring an amount of a High-Z additive provided in a material.

BACKGROUND OF THE INVENTION

High-Z (high atomic weight) materials are used in coatings and fillers in the Continuous Web Solution (CWS) market that provide flat sheet materials, e.g., rubbers, plastics, metals and hybrid materials, e.g., organic materials including High-Z material additives. Typically these are expensive materials and it is of interest to control the amount of High-Z material used very carefully. Online measurements are therefore required. Currently, dual-point (subtractive) techniques using two scanners (implementing sensors) are used to measure the amount of an additive and are typically an expensive solution.

It would be advantageous to provide a single-point measurement technique for non-destructive measurement of an amount of high-Z material (e.g., a heavy metal) in such flat sheet materials.

SUMMARY OF THE INVENTION

A single-point measurement technique of high-Z additives in a flat sheet material implements a nuclear and an x-ray sensor and a calibrating technique using both signals simultaneously. The measurement is a less expensive solution and requires a single scanner only. One embodiment of the invention implements two standard sensors in a standard dual head arrangement. A novel algorithm executed in software is required to process the data obtained from the sensors. The technique can be used for a variety of high-Z additives and does not rely on tuning operating conditions, as is the case for the ash sensor in use in the paper manufacturing industry.

Thus, according to a first aspect of the invention, there is provided a single-point measurement apparatus for determining a concentration of a high-Z material in a material sample comprising:

first and second sensor devices for receiving a material sample and scanning the material sample with a first sensor device that is ash insensitive for generating a first sensor response signal and a second sensor device that is sensitive to presence of high-Z material and generating a second sensor response signal; and, means of receiving both first and second sensor response signals simultaneously from the first and second sensor devices and processing the data obtained from the first and second sensor response signals to extract a weight of the high-Z material additive, wherein the weight of the high-Z material additive is determined in a single scan of the material sample.

The high-Z material is a heavy metal and typically comprise Platinum (Pt) although other high-Z materials may be used including: Ruthenium, Calcium, Titanium, Aluminum, Iron, Silicon, and similar metals. Preferably, the first sensor device is a nuclear-based sensor gauge e.g., comprising material selected from the following: Kr-85, Sr-90 or Pm-147 or Am-241. The second sensor device is an X-ray sensor. Preferably, the first and second sensor devices are housed in a dual head design adapted for scanning a material sample in a single scan.

Further to the single-point measurement apparatus, both sensor signals obtained from the first and second sensor devices are simultaneously processed according to logic implemented for calculating the basis weight of the High-Z material ("M") according to:

$$M = C + A_1 \times \ln(R_{Kr}) + A_2 \times \ln(R_{Kr})^2 + B_1 \times \ln(R_{Xray}) + B_2 \times \ln(R_{Xray})^2 + D \times \ln(R_{Kr}) \times \ln(R_{Xray})$$

where $R_i$ is a sensor ratio for each said first and second sensor device, and C, $A_i$, $B_i$, and D are determined constants. Preferably, the C, $A_i$, $B_i$, and D constants are determined using samples with known amounts of high-Z additive, the system measuring the samples, recording the resulting sensor outputs, and fitting the sensor readings to the known amounts of additive to determine the coefficients.

According to a further aspect of the invention, there is provided a single-point measurement method and computer program product comprising steps of:

receiving a material sample and scanning the material sample with a first sensor device that is ash insensitive for generating a first sensor response signal and a second sensor device that is sensitive to presence of high-Z material and generating a second sensor response signal; and, processing both first and second sensor response signals simultaneously from the first and second sensor devices to extract a weight of the high-Z material additive, wherein the weight of the high-Z material additive is determined in a single scan of the material sample.

BRIEF DESCRIPTION OF THE DRAWINGS

These and other objects, features and advantages of the present invention will become apparent from the following detailed description of illustrative embodiments thereof, which is to be read in connection with the accompanying drawings, in which.

DETAILED DESCRIPTION OF THE INVENTION

The present invention is directed to a novel measurement technique for measuring a concentration of High-Z (heavy metal) materials in a flat sheet of polymer or carbon-based fibre (organic) material. The invention could also be used to measure the amount of organic additive in a generally high-Z material (e.g., polymer-based resins in glass mat).

Figure 1:
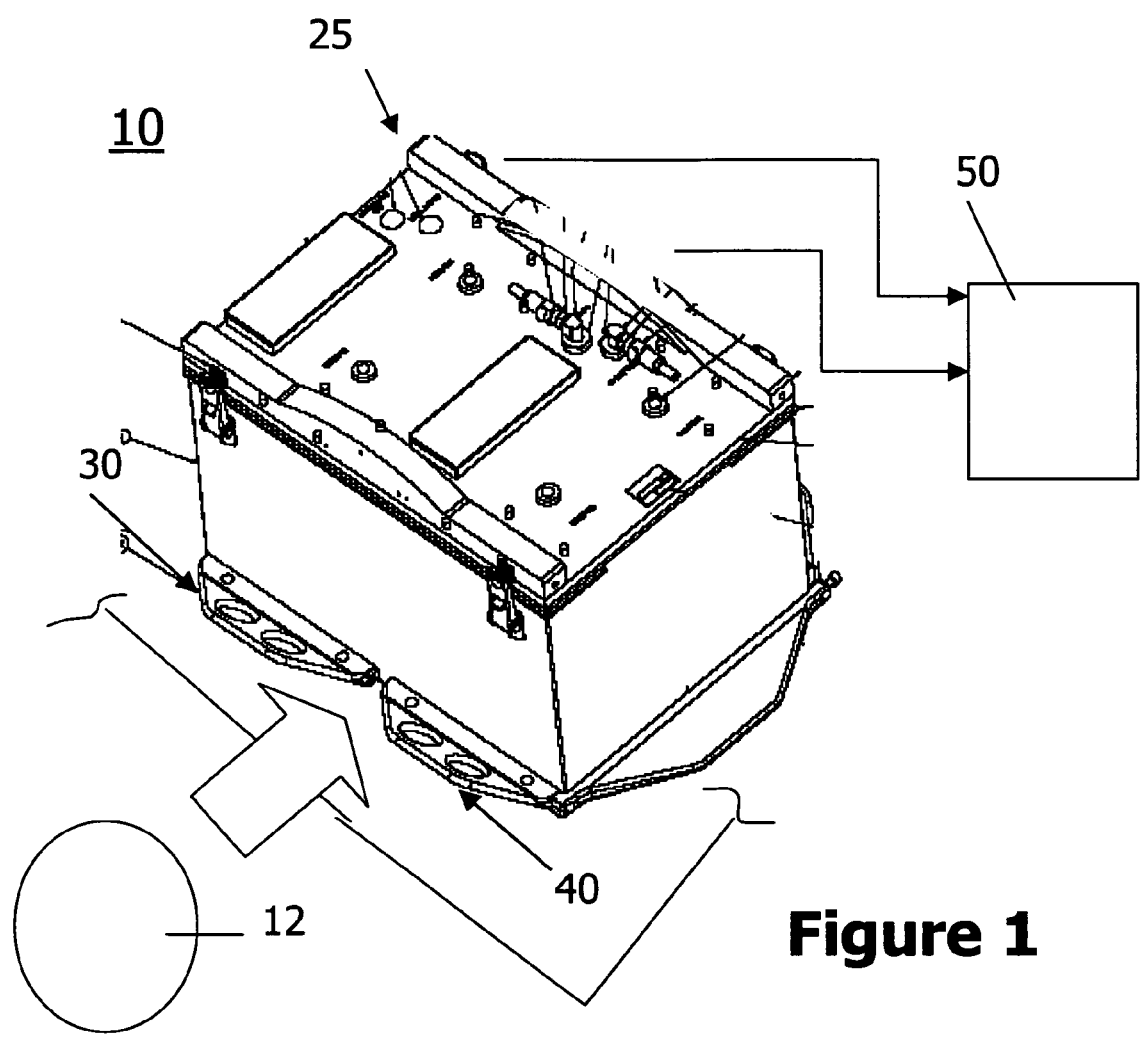
FIG. 1 is a diagram of the system including the dual head High-Z sensor in which the present invention is implemented.

FIG. 1 is a diagram of the system 10 including a dual-head High-Z sensor assembly 25 in which the present invention is implemented. The dual-head sensor comprises a standard nuclear-based sensor device 30 and an X-ray-based sensor device 40. The system 10, according to the invention, is programmed to measure the amount of a high-Z material (e.g., a heavy metal such as Pt) in a flat sheet product or sample 12. In one example embodiment, the dual-head sensor assembly 25 is available from Honeywell (model no. 4623-04; scanner model no. 2080-03) and includes a high-ash insensitive $^{85}$Kr gauge (e.g., Honeywell sensor model no. 4203-03) and a 5 kV x-ray absorption gauge (e.g., Honeywell sensor model no. 4217-00), for example. Respective sensor ratio outputs 35, 45 of the dual-head sensor 25 are input to a processor means 50 (e.g. a computer workstation, mobile device or PC) that executes software for implementing logic required to perform the inter-gauge calibration according as will be described in greater detail herein. It is understood that the logic implemented may be applied to any pair (x-ray and nuclear) of sensors selected from the following Honeywell products (all of which are existing and would require no changes to any hardware): e.g., x-ray sensor Honeywell model nos. 4217-01, 4217-02, 4217-00; and, nuclear sensor Honeywell model nos: 4203-00, 4203-01, 4203-02, 4203-03, 4203-13, 4203-04, 4203-05, 4203-07, 4203-08, 4203-09. These example nuclear sensor devices implement contents including, but not limited to: Krypton-85, Strontium-90, Promethium-147 and Americium-241. Further to FIG. 1, an open draw is required to perform the measurement on the samples 12; the minimum opening required is 5 cm (e.g., enough to accommodate the sensor spots (the sensitive areas of the detectors in both receiver and source), but typically range between 0.4 inches and 1.0 inches in the example embodiment described herein.

For purposes of explanation, the measurements for determining high-Z concentrations are performed on flat sheet materials or samples thereof such as, for example, those having a carbon-fibre based or polymer—(e.g., light organics) based coating having a High-Z material additive (e.g., Platinum (Pt), Ruthenium (Ru), Aluminum (Al), Silicon (Si), Calcium (Ca), Titanium (Ti), Iron (Fe)). As will become clearly evident, system 10 provides a measurement that is a less expensive solution than a differential nuclear measurement, as it only requires a single scan.

Particularly, a single-point measurement of high-Z additives in a flat sheet material combines the nuclear and an x-ray sensor outputs and implements a calibrating technique using both signals simultaneously. The novel algorithm provided in software executed by computer device 50 processes the data obtained from both the nuclear-based 30 and X-ray-based 40 sensor devices. The technique can be used for a variety of high-Z additives and does not rely on tuning operating conditions, as is the case for an "ash" sensor product as used in the paper industry. The software performs method steps implementing the algorithm for calculating the weight of the High-Z material component in the sample. In one embodiment, the formula for calculating the weight of the High-Z material ("M") is as set forth in the following equation:

$$M = C + A_1 \times \ln(R_{Kr}) + A_2 \times \ln(R_{Kr})^2 + B_1 \times \ln(R_{Xray}) + B_2 \times \ln(R_{Xray})^2 + D \times \ln(R_{Kr}) \times \ln(R_{Xray})$$

where $R_i$ is a sensor ratio for each gauge, and $C$, $A_i$, $B_i$, and $D$ are constants to be determined.

EXAMPLES

The present invention is now described by way of an example measurement of samples from a flat sheet of carbon-fibre based material or Polymer based material coatings to determine an amount of a material, e.g., Platinum (Pt), Ruthenium (Ru), Aluminum (Al), Silicon (Si), Calcium (Ca), Titanium (Ti), or Iron (Fe)) in the coating. In a first example, a polymer-based material sample is provided, particularly, a polymer-based sheet coated with a carbon/Nafion®/Pt paste (Nafion® is a trademark of E.I. Du Pont de Nemours and company and is a polymer material consisting of light atoms such as H, C, F and O "low-Z" material). In the illustrative embodiment, about twelve (12) such polymer-based product samples were provided, each sample comprising, for example, a circle stamped out of the polymer-backed product, with each having a different amount of high-Z material (e.g., Pt). In the example embodiment described, the diameter of the circle was 4.5" but this sample size is not critical to the invention. Each sample is shot in the "dual head" sensor device 25 shown in FIG. 1 while moving the samples around, e.g., in a rotatable platform (not shown) in order to provide some amount of averaging over the sample. In this first example, the circular samples are spun in a suitable mechanical sample holder known to those skilled in the art, and the sensor ratios were recorded. Table 1 provides the results obtained from the first polymer-based sample set including: the output sensor ratios from both the 5 kV x-ray sensor and a $^{85}$Kr (high-ash insensitive) sensor. The "sensor ratio" is a ratio of the (nuclear-based or X-ray-based) detector (sensor) signal without the sample 12 in the detector 25 and then with the sample 12 in the detector. The ratio of the detector (sensor) signal with and without the sheet is the sensor response and those values are recorded.

As can be seen in Table 1, the output of the implemented algorithm includes the calculated basis weight of the high Z material (e.g., Pt) in mass per unit area, or "basis weight". The results are as follows:

TABLE 1

| Pt wt (mg/cm$^2$) | $^{85}$Kr sensor ratio | 5 keV x-ray sensor ratio |
|---|---|---|
| 0.448 | 0.717 | 0.371 |
| 0.441 | 0.720 | 0.383 |
| 0.474 | 0.715 | 0.364 |
| 0.471 | 0.715 | 0.367 |
| 0.391 | 0.723 | 0.399 |
| 0.392 | 0.724 | 0.402 |
| 0.230 | 0.742 | 0.493 |
| 0.229 | 0.741 | 0.490 |
| 0.248 | 0.740 | 0.478 |
| 0.245 | 0.739 | 0.478 |
| 0.197 | 0.745 | 0.508 |
| 0.199 | 0.746 | 0.508 |

In a second example, a carbon-based material sample is provided; particularly, a carbon-fibre based sheet coated with a carbon/Nafion®/Pt paste. In this example, nine (9) samples having carbon-fibre based backing, coated with carbon/Nafion®/Pt paste were provided, each with a different amount of Pt. Table 2 provides the results obtained from the carbon-fiber based sample set including: the output sensor ratios from both the 5 keV x-ray sensor and the $^{85}$Kr (high-ash insensitive) sensor. As can be seen in Table 2, the output of the implemented algorithm includes the calculated basis weight of the high-Z material (e.g., Pt) in mass per unit area. The results are as follows:

TABLE 2

| Pt wt (mg/cm$^2$) | $^{85}$Kr sensor ratio | 5 keV x-ray sensor ratio |
|---|---|---|
| 0.18 | 0.594 | 0.443 |
| 0.32 | 0.604 | 0.399 |
| 0.38 | 0.450 | 0.218 |
| 0.40 | 0.455 | 0.216 |
| 0.42 | 0.595 | 0.365 |
| 0.54 | 0.541 | 0.294 |
| 0.57 | 0.556 | 0.289 |
| 0.57 | 0.451 | 0.204 |
| 0.61 | 0.441 | 0.189 |

As can be concluded from the results of Tables 1 and 2, the $^{85}$Kr sensor is less sensitive to the presence of heavy metals (such as Pt) than the x-ray sensor. The $^{85}$Kr sensor will therefore measure the total basis weight quite accurately. The x-ray sensor, on the other hand, is very sensitive to heavy atoms and will give a very different response to samples containing different levels of high-Z material, e.g., Pt. Used together, these two sensors enable measurement of the Pt in each sample; the Pt being measured by the x-ray sensor and the nuclear gauge providing a "correction" for variations in backing material and paste.

Fitting the logarithm of the sensor ratios to the lab Pt weight:

$$M_{Pt} = C + A_1 \times \ln(R_{Kr}) + A_2 \times \ln(R_{Kr})^2 + B_1 \times \ln(R_{Xray}) + B_2 \times \ln(R_{Xray})^2 + D \times \ln(R_{Kr}) \times \ln(R_{Xray})$$

where $R_i$ is the sensor ratio determined for each X-ray and Kr gauge, and C, $A_i$, $B_i$, and D are the coefficients to be determined. The coefficients in the formula are determined on a case-by-case (application-specific) basis. Using samples with known amounts of high-Z additive, experiments are run to measure them, record the resulting sensor outputs, and fit the sensor readings to the known amounts of additive, e.g., using a least squares minimization technique The fitting process determines the coefficients. The "M" and all other constants in the formula are in mass per unit area e.g., mg/cm². If one assumes uniform additive density, one can fit in length units instead (m, cm, etc)—in this case, M and all constants would be in units of length.

Table 3 illustrates the resulting calibration coefficients obtained for the polymer-based samples and, and Table 4 illustrates the resulting calibration coefficients obtained for the carbon-fibre-based samples in the example depicted.

TABLE 3

|   | value | error |
|---|---|---|
| C | −2.2 | 1 |
| $A_1$ | −12 | 8 |
| $A_2$ | −15 | 13 |
| $B_1$ | 0 | 0 |
| $B_2$ | 0.3 | 0.1 |
| D | 0 | 0 |

TABLE 4

|   | value | error |
|---|---|---|
| C | 0 | 0 |
| $A_1$ | −1.28 | 0.09 |
| $A_2$ | −3.4 | −0.3 |
| $B_1$ | 0 | 0 |
| $B_2$ | 0.68 | 0.06 |
| D | 0 | 0 |

Figure 2:
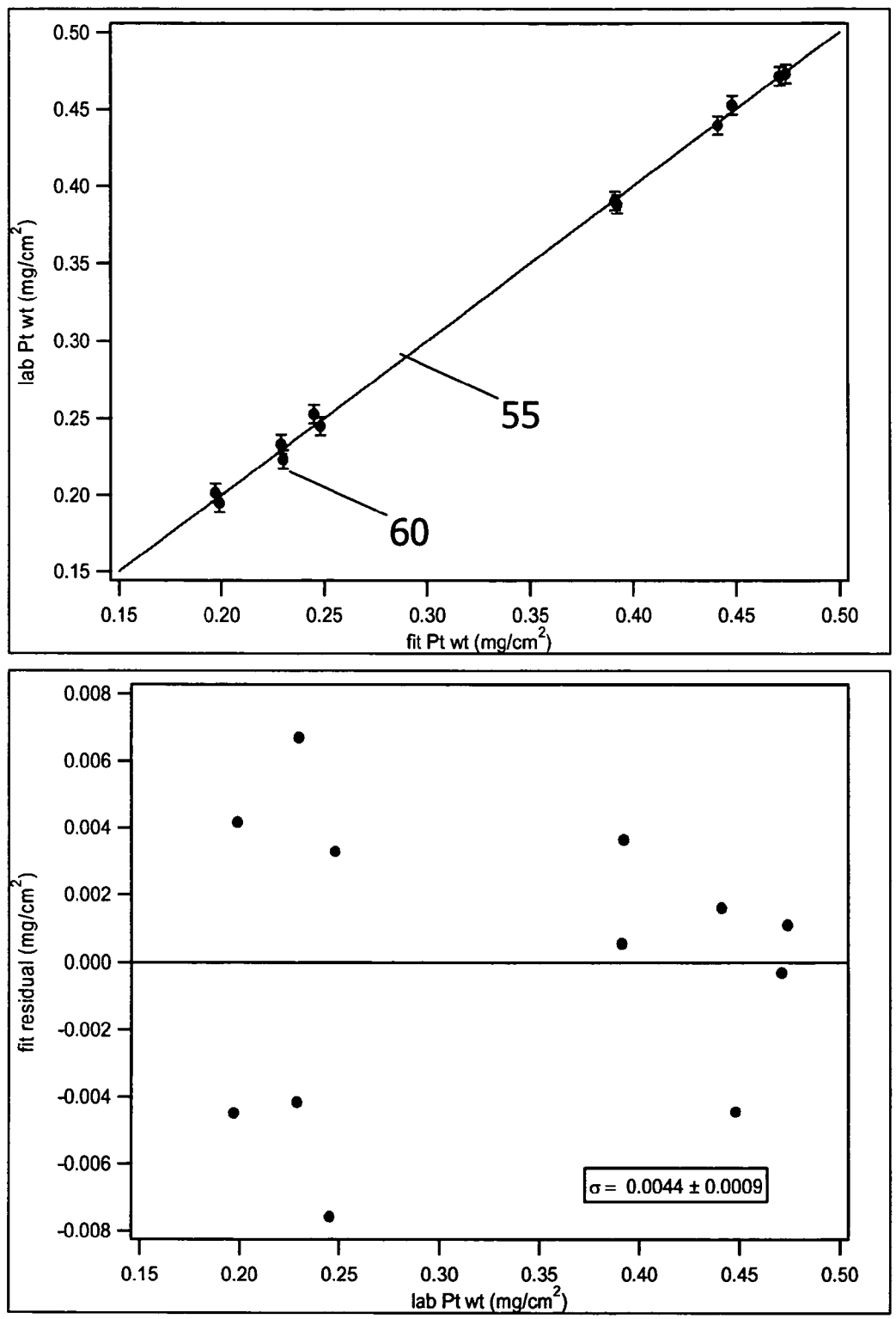
FIGS. 2 and 3 depict calibration results for respective polymer-based samples (FIG. 2) and carbon-fibre-based samples (FIG. 3); and, FIG. 4 depicts calibration results for polymer-based samples having varied amounts of Pt::carbon/polymer (Nafion®) ratio.
Figure 3:
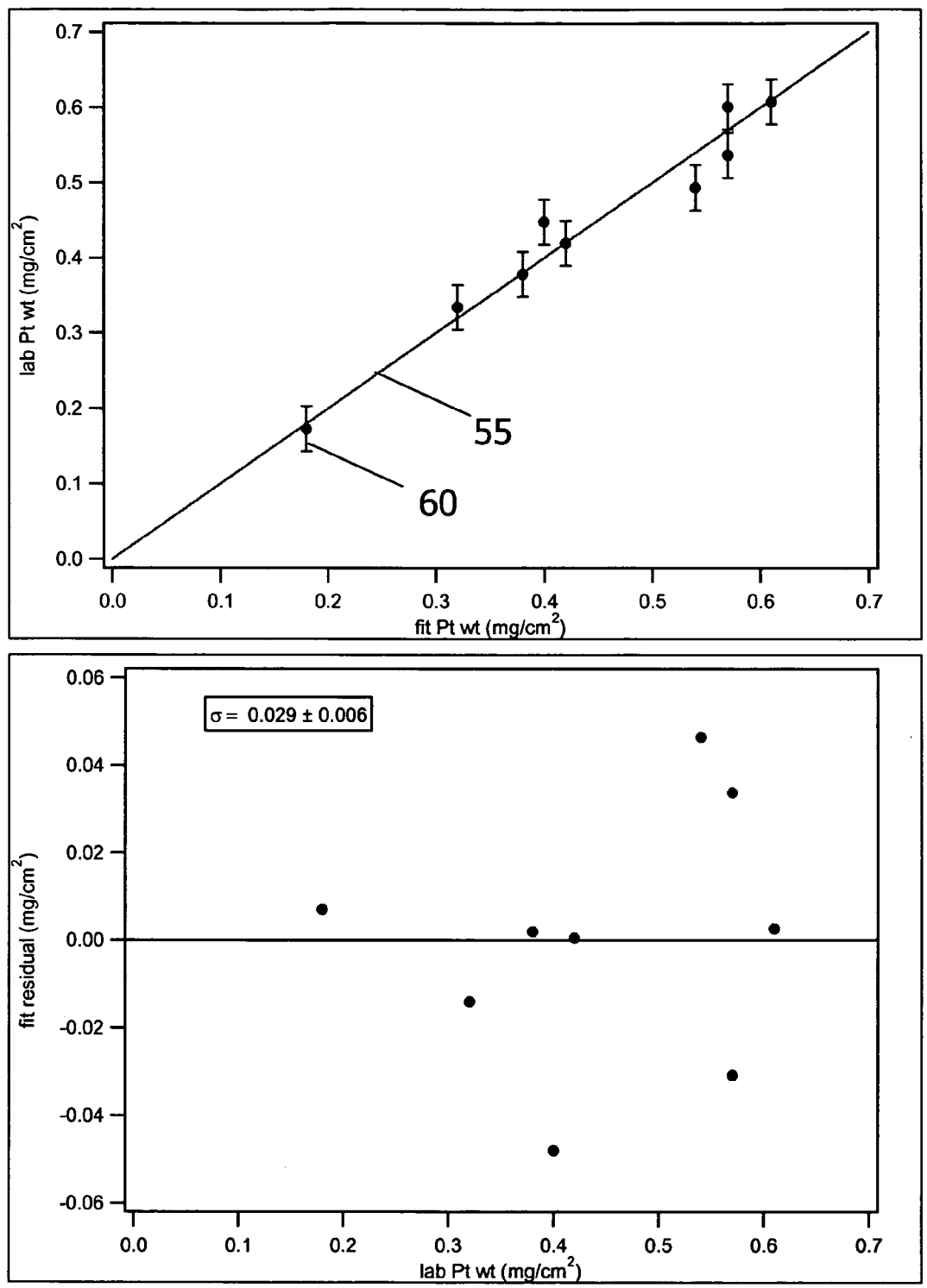

The calibration results are illustrated in respective FIGS. 2 and 3. The diagonal lines 55 are not fits but provide a guide (a perfect fit falls exactly along the 45° line).

From FIG. 2, it is seen that for the polymer-backed samples, the two sensors provide enough information to extract the weight of the Pt with an estimated calibration accuracy of approximately 0.0044 mg/cm², or about 1.25% (out of 0.35 mg/cm² total Pt weight). From FIG. 3, the calibration accuracy results for the carbon-fiber backed samples are about 0.029 mg/cm², or about 8% (out of 0.35 mg/cm² total Pt weight. The difference between these results is due to the more consistent nature of the polymer base—the backing is more uniform, so that the only variation is really due to the additional Pt in the paste.

During production, variations in the paste-to-Pt ratio will likely occur. To examine the sensitivity of the measurement to the exact ratio of carbon/Nafion® to Pt in the paste, the amount of carbon/Nafion® is artificially increased, for example, by stacking polymer-backed non-Pt samples on the Pt-bearing samples, shooting the resulting stack with x-rays, obtaining the sensor responses, and including them in the fit. By stacking, the amount of polymer backing plus paste is increased by about a factor of 3—a much larger range than would be likely to occur in production.

Figure 4:
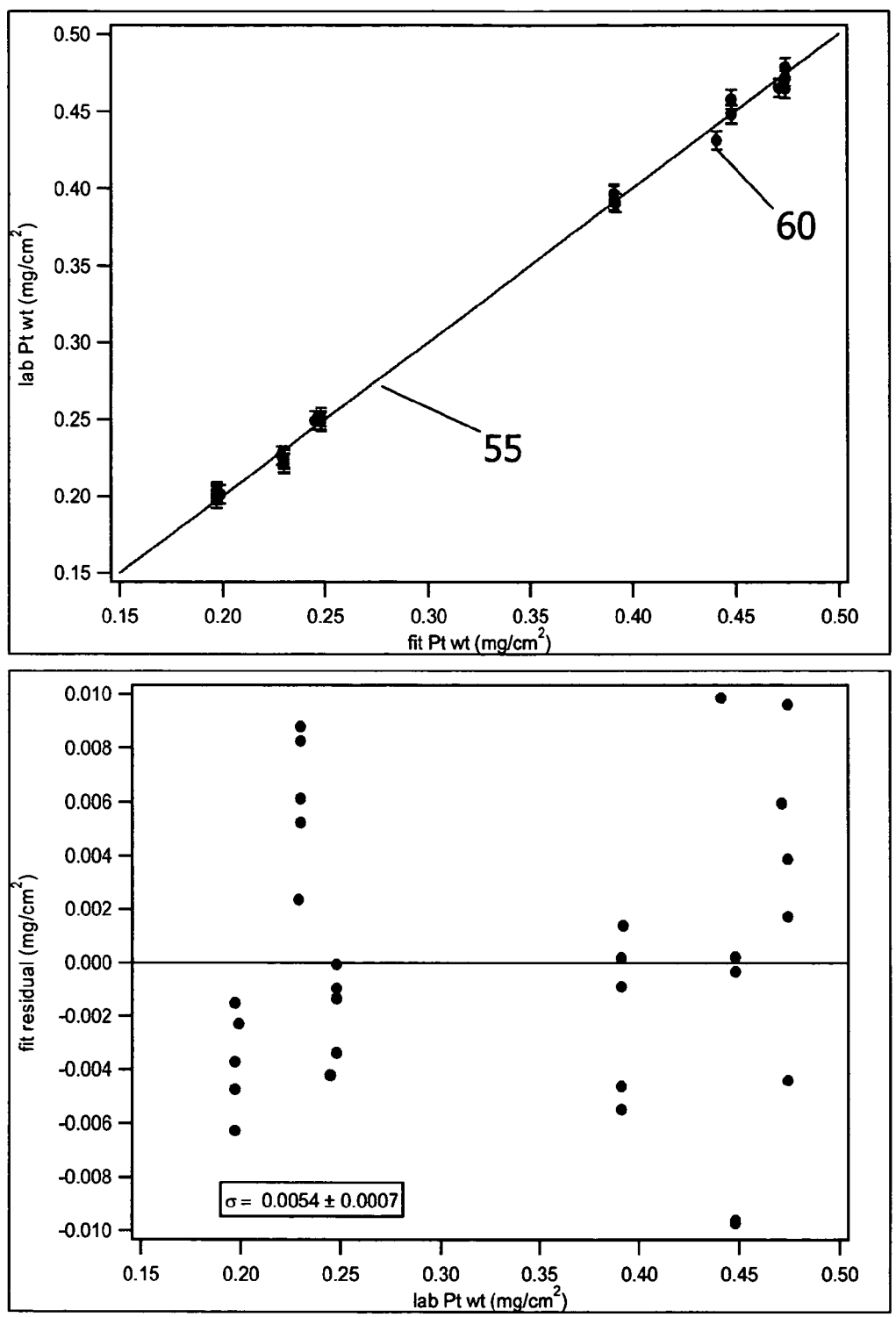

An additional step is performed to obtain and include the readings of the nuclear sensor in order to achieve a good fit—the nuclear gauge corrects for the additional paste and backing. The results are shown in Table 5 and FIG. 4. The calibration accuracy is about 1.5% of the total Pt weight. Table 5 particularly provides the determined fit coefficients for polymer bases samples having varied Pt::carbon/Nafion® ratio.

TABLE 5

|   | Value | error |
|---|---|---|
| C | −0.046 | 0.011 |
| $A_1$ | 1.454 | 0.028 |
| $A_2$ | 0.158 | 0.016 |
| $B_1$ | −0.959 | 0.027 |
| $B_2$ | 0.020 | 0.010 |
| D | 0.000 | 0.000 |

In order to complete the analysis in a consistent way, errors have been deduced for the real example laboratory Pt weights. For the polymer-backed samples, an error of approximately 0.006 mg/cm² in the Pt weight has been deduced (note that the Pt weights for these samples were provided to 0.001 mg/cm²). The error inferred for the carbon-fibre backed samples is 0.03 mg/cm² (the Pt weights for these samples were provided to 0.01 mg/cm²). These errors are inferred by requiring the correct $\zeta^2$ value for the fits. They are illustrated by the error bars 60 in the FIGS. 2-4.

Because the same sensors were used to measure each type of product (each product contains approximately the same amount of Pt, but gives rather different results), it is assumed that the dominant cause of calibration uncertainty is the samples themselves, i.e., all of the measurement error are ascribed to uncertainty in the Pt weight of the provided samples. One could, in principle, check the supplied Pt weights by burning the samples in a furnace and weighing the resulting ash (which is assumed to be nothing but pure Pt).

Another source of error is due to the uniformity of the Pt on the samples. If the Pt is not uniformly distributed over the surface of the samples, the difference between the surface areas measured becomes significant—the sensor averages over a much smaller region than a weigh scale. To test this, the system of FIG. 1 was implemented to provide a "one shot" of the carbon-fiber sheets in the sensor in 10 different locations. The results shown in Table 6 depict the uniformity of carbon-fiber backed samples and the corresponding x-ray sensor ratios.

As shown in Table 6, the variation of only 1.3% in this sample indicates that non-uniformity is not what is limiting the accuracy of the calibration for the carbon-fiber sheets. Again, this points to a general uncertainty in the exact Pt content of the coatings.

TABLE 6

|    | x-ray ratio |
|----|-------------|
| 1  | 0.213495 |
| 2  | 0.217001 |
| 3  | 0.210815 |
| 4  | 0.215596 |
| 5  | 0.213819 |
| 6  | 0.213590 |
| 7  | 0.212740 |
| 8  | 0.211693 |
| 9  | 0.211392 |
| 10 | 0.206844 |
| average | 0.213 |
| st dev | 0.003 |
| st dev, % | 1.31 |

It has been demonstrated that a calibration accuracy of about 1.5% in Pt weight is possible on the polymer-backed product, and about 8% in Pt weight on the carbon-fiber backed grade. It is assumed that with better calibration samples, the absolute accuracy might be improved, e.g., likely better than 1% with relative, or scanning (profile) data. Other heavy coatings (ex. those containing Ruthenium) would likely require separate calibrations. Sample sets like those provided for the example study provided herein would be required to calibrate the sensors, for all types of product a customer wishes to measure.

The present invention may be used to measure specific high-Z material in a variety of materials/application. Example applications in which the single point measuring technique of the invention may be implemented include, but are not limited to: fiberglass mats with resin binder (organic) and polyester fibers (the glass and organics might be separately measured by the technique of the invention); plastic sheet with embedded metallic flake (the flake and plastic weights may be measured separately); and, plastic sheet with a "whitening" agent, e.g., titanium dioxide and/or calcium carbonate (invention may be used to measure the whitening agent concentration).

While the invention has been particularly shown and described with respect to illustrative and preformed embodiments thereof, it will be understood by those skilled in the art that the foregoing and other changes in form and details may be made therein without departing from the spirit and scope of the invention which should be limited only by the scope of the appended claims.

What is claimed is:

1. A single-point measurement apparatus for determining a concentration of a high-Z material in a flat sheet material sample comprising:
   a first nuclear-based sensor device and a second X-ray sensor device for receiving said flat sheet material sample and scanning said flat sheet material sample with electrons for sensing by said first nuclear-based sensor device that is substantially ash insensitive for generating a first sensor response signal and radiation for sensing by said second X-ray sensor device that is sensitive to presence of high-Z material and generating a second sensor response signal; and
   means for receiving both first and second sensor response signals simultaneously from said first nuclear-based and second X-ray based sensor devices and processing the data obtained from the first and second sensor response signals to extract a weight of the high-Z material additive, the weight of the high-Z material additive being determined in a single scan of the flat sheet material sample,
   wherein said means for receiving both signals simultaneously from said first and second sensor devices and processing the data implements logic for calculating the weight of the High-Z material ("M") according to:

$$M = C + A_1 \times \ln(R_{Kr}) + A_2 \times \ln(R_{Kr})^2 + B_1 \times \ln(R_{Xray}) + B_2 \times \ln(R_{Xray})^2 + D \times \ln(R_{Kr}) \times \ln(R_{Xray})$$

where $R_i$ is a sensor ratio for each said first and second sensor device, and $C$, $A_i$, $B_i$, and $D$ are determined constants.

2. The single-point measurement apparatus as claimed in claim 1, wherein said high-Z material is a heavy metal.

3. The single-point measurement apparatus as claimed in claim 1, wherein said high-Z material comprises one selected from the group of Pt, Ru, Al, Fe, Si, Ca, Ti.

4. The single-point measurement apparatus as claimed in claim 1, wherein said nuclear-based sensor gauge comprises material selected from the following: Kr-85, Sr-90, Pm-147 or Am-241.

5. The single-point measurement apparatus as claimed in claim 1, wherein said first and second sensor devices are housed in a dual head design adapted for scanning a material sample in a single scan.

6. The single-point measurement apparatus as claimed in claim 1, wherein said $C$, $A_i$, $B_i$, and $D$ constants are determined using samples with known amounts of high-Z additive, said system measuring said samples, recording the resulting sensor outputs, and fitting the sensor readings to the known amounts of additive to determine the coefficients.

7. The single-point measurement apparatus as claimed in claim 1, wherein said material sample comprises a sheet of material.

8. The single-point measurement apparatus as claimed in claim 7, wherein said sheet of material includes a polymer backing.

9. The single-point measurement apparatus as claimed in claim 7, wherein said sheet of material includes a carbon-fibre based backing.

10. A method for determining a concentration of a high-Z material in a flat sheet material sample comprising:
    receiving a material sample and scanning said flat sheet material sample with electrons for sensing by a first nuclear-based sensor device that is substantially ash insensitive for generating a first sensor response signal and radiation for sensing by a second X-ray sensor device that is sensitive to presence of high-Z material and generating a second sensor response signal; and,
    processing both first and second sensor response signals simultaneously from said first nuclear-based and second X-ray sensor devices to extract a weight of the high-Z material additive, wherein the weight of the high-Z material additive is determined in a single scan of the flat sheet material sample, wherein said means for receiving both signals simultaneously from said first and second sensor devices and processing the data implements logic for calculating the weight of the High-Z material ("M") according to:

$$M = C + A_1 \times \ln(R_{Kr}) + A_2 \times \ln(R_{Kr})^2 + B_1 \times \ln(R_{Xray}) + B_2 \times \ln(R_{Xray})^2 + D \times \ln(R_{Kr}) \times \ln(R_{Xray})$$

where $R_i$ is a sensor ratio for each said first and second sensor device, and $C$, $A_i$, $B_i$, and $D$ are determined constants.

11. The method as claimed in claim 10, wherein said high-Z material is a heavy metal.

12. The method as claimed in claim 11, wherein said heavy metal comprises one selected from the group of Pt, Ru, Al, Fe, Si, Ca, Ti.

13. The method as claimed in claim 10, wherein said nuclear-based sensor gauge comprises material selected from the following: Kr-85, Sr-90, Pm-147 or Am-241.

14. The method as claimed in claim 10, wherein said first and second sensor devices are housed in a dual head design adapted for scanning a material sample in a single scan.

15. The method as claimed in claim 10, wherein said C, $A_i$, $B_i$, and D constants are determined using samples with known amounts of high-Z additive, said system measuring said samples, recording the resulting sensor outputs, and fitting the sensor readings to the known amounts of additive to determine the coefficients.

16. A program storage device readable by a machine, tangibly embodying a program of instructions executable by the machine to perform method steps for determining a concentration of a high-Z material in a flat sheet material sample, said method steps comprising:

receiving a flat sheet material sample and scanning said flat sheet material sample with electrons for sensing by a first nuclear-based sensor device that is substantially ash insensitive for generating a first sensor response signal and radiation for sensing by a second X-ray sensor device that is sensitive to presence of high-Z material and generating a second sensor response signal; and, processing both first and second sensor response signals simultaneously from said first nuclear-based and second X-ray sensor devices to extract a weight of the high-Z material additive, wherein the weight of the high-Z material additive is determined in a single scan of the material sample, wherein said means for receiving both signals simultaneously from said first and second sensor devices and processing the data implements logic for calculating the weight of the High-Z material ("M") according to:

$$M = C + A_1 \times \ln(R_{Kr}) + A_2 \times \ln(R_{Kr})^2 + B_1 \times \ln(R_{Xray}) + B_2 \times \ln(R_{Xray})^2 + D \times \ln(R_{Kr}) \times \ln(R_{Xray})$$

where $R_i$ is a sensor ratio for each said first and second sensor device, and C, $A_i$, $B_i$, and D are determined constants.

* * * * *